United States Patent
Kelley

(10) Patent No.: US 7,314,502 B2
(45) Date of Patent: Jan. 1, 2008

(54) METHOD AND SYSTEM FOR SEPARATING A COMPONENT FROM A MULTI-COMPONENT GAS

(75) Inventor: Bruce T. Kelley, Kingwood, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 492 days.

(21) Appl. No.: 10/526,099

(22) PCT Filed: Jun. 30, 2003

(86) PCT No.: PCT/US03/20625

§ 371 (c)(1),
(2), (4) Date: Feb. 25, 2005

(87) PCT Pub. No.: WO2004/028665

PCT Pub. Date: Apr. 8, 2004

(65) Prior Publication Data

US 2006/0162554 A1 Jul. 27, 2006

(51) Int. Cl.
*B01D 53/22* (2006.01)
(52) U.S. Cl. .................... 95/45; 95/51; 96/4; 96/8; 96/10; 96/11
(58) Field of Classification Search .............. 95/45, 95/46, 47, 49, 50, 51, 52, 53, 54, 55, 29; 96/4, 6, 7, 8, 10, 11; 210/640
See application file for complete search history.

(56) References Cited

U.S. PATENT DOCUMENTS

| | | | |
|---|---|---|---|
| 3,735,558 A | 5/1973 | Skarstrom et al. ............ 55/16 |
| 3,832,830 A | 9/1974 | Gerow ..................... 55/158 |
| 4,019,868 A | 4/1977 | Sebacher et al. ............. 23/281 |
| 4,031,012 A | 6/1977 | Gics ..................... 210/321 A |
| 4,666,469 A * | 5/1987 | Krueger et al. .................. 96/8 |
| 5,013,437 A * | 5/1991 | Trimmer et al. ................. 96/8 |
| 5,084,073 A | 1/1992 | Prasad ..................... 55/16 |
| 5,137,547 A | 8/1992 | Chretien ..................... 55/16 |
| 5,183,486 A | 2/1993 | Gatten et al. ................. 55/159 |
| 5,820,654 A * | 10/1998 | Gottzman et al. ............. 96/11 |
| 6,280,502 B1 | 8/2001 | van Veen et al. ............... 95/29 |
| 6,293,084 B1 | 9/2001 | Drnevich et al. .......... 60/39.02 |
| 6,513,345 B1 | 2/2003 | Betting et al. ................ 62/637 |
| 6,540,817 B1 * | 4/2003 | Hachimaki ..................... 96/10 |
| 6,558,450 B2 * | 5/2003 | Sengupta et al. ................. 96/8 |
| 2005/0092683 A1* | 5/2005 | Goldsmith ..................... 96/11 |

OTHER PUBLICATIONS

International Search Report for PCT/US03/20625, mailed Dec. 11, 2003, 5 pages.
International Preliminary Examination Report for PCT/US03/20625, mailed Oct. 13, 2004, 11 pages.
PCT Written Opinion for PCT/US03/20625, mailed Jul. 9, 2004, 5 pages.

* cited by examiner

*Primary Examiner*—Jason M. Greene

(57) ABSTRACT

A method and apparatus for separating a component from a multi-component feed gas stream has a flow conduit (14) having a semi-permeable section (15) that permeates the component to be separated from feed gas stream (12). A sweep gas is provided at a first velocity on the permeate sides of flow conduit (14) and the velocity of sweep gas (13) is accelerated so that the velocity of sweep gas (13) along at least a portion of the permeate side of flow conduit (14) is greater than the first velocity. The mixture of permeate and sweep gas (13) is then decelerated by diffuser (20), thereby recovering as pressure a portion of the energy of feed gas stream (12).

9 Claims, 3 Drawing Sheets

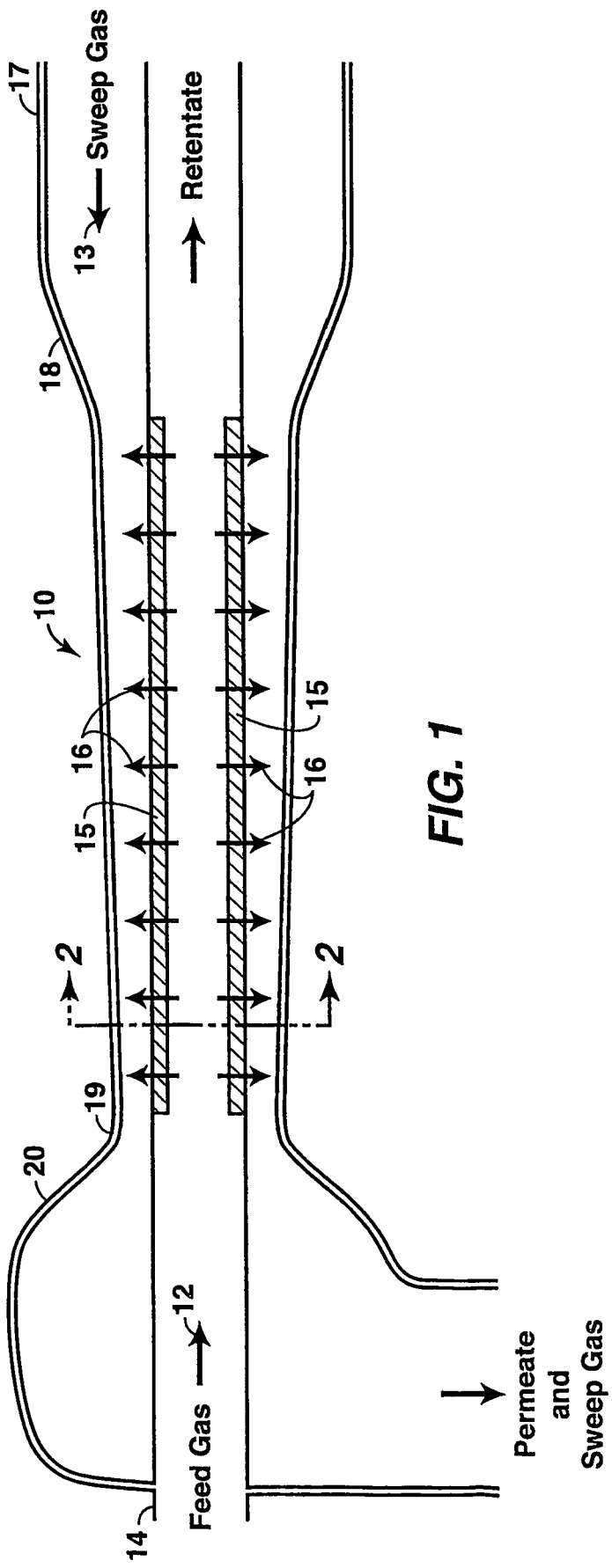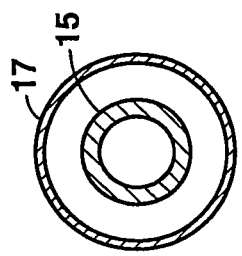

METHOD AND SYSTEM FOR SEPARATING A COMPONENT FROM A MULTI-COMPONENT GAS

FIELD OF THE INVENTION

The present invention relates generally to a semi-permeable, gas-separation system for separating one or more components from a multi-component gas.

BACKGROUND OF THE INVENTION

Natural gas is an important fuel gas and it is used extensively as a basic raw material in the petrochemical and other chemical process industries. The composition of natural gas varies widely from field to field. Many natural gas reservoirs contain relatively low percentages of hydrocarbons (less than 40%, for example) and high percentages of acid gases, principally carbon dioxide, but also hydrogen sulfide, carbonyl sulfide, carbon disulfide and various mercaptans. Removal of acid gases from natural gas produced in remote locations is desirable to provide conditioned or sweet, dry natural gas either for delivery to a pipeline, natural gas liquids recovery, helium recovery, conversion to liquefied natural gas (LNG), or for subsequent nitrogen rejection. $H_2S$ is removed because it is toxic in minute amounts and it is corrosive in the presence of water through the formation of hydrosulfurous acid. Upon combustion, $H_2S$ forms sulfur dioxide, a toxic and corrosive compound. $CO_2$ is also corrosive in the presence of water, and it can form dry ice, hydrates and can cause freeze-up problems in pipelines and in cryogenic equipment often used in processing natural gas. Also, by not contributing to the heating value, $CO_2$ merely adds to the cost of gas transmission.

An important aspect of any natural gas treating process is economics. Natural gas is typically treated in high volumes, making even slight differences in capital and operating costs of the treating unit significant factors in the selection of process technology. Some natural gas resources are now uneconomical to produce because of processing costs. There is a continuing need for improved natural gas treating processes that have high reliability and represent simplicity of operation.

A number of processes for the recovery or removal of carbon dioxide from gas steams have been proposed and practiced on a commercial scale. The processes vary widely, but generally involve some form of solvent absorption, adsorption on a porous adsorbent, distillation, or diffusion through a semipermeable membrane.

Membranes are thin barriers that allow preferential passage of certain components of a multi-component gas mixture. Most membranes can be separated into two types; porous and nonporous. Porous membranes separate gases based on molecular size and/or differential adsorption by small pores in the membrane. Gas separation membranes used in natural gas applications are often nonporous or asymmetric and separate gases based on solubility and diffusivity. These membranes typically have a microporous layer, one side of which is covered with a thin, nonporous "skin" or surface layer. The separation of the gas mixtures through an asymmetric membrane occurs in its skin, while the microporous substrate gives the membrane mechanical strength.

In a typical membrane separation process, a gas is introduced into the feed side of a module that is separated into two compartments by the permeable membrane. The gas stream flows along the surface of to membrane and the more permeable components of the gas pass through the membrane barrier at a higher rate than those components of lower permeability. After contacting the membrane, the depleted feed gas residue stream, retentate, is removed from contact with the membrane by a suitable outlet on the feed compartment side of the module. The gas on the other side of the membrane, the permeate, is removed from contact with the membranes the permeate side, through a separate outlet. The permeate stream from the membrane may be referred to as being "enriched" in the readily permeable components relative to the concentration of the readily permeable components in the retentate stream. The retentate may also be referred to as being "depleted" of the readily permeable components. While the permeate stream can represent the desired product, in most natural gas permeation processes the desired product is the retentate stream, and the permeate stream comprises contaminants such as $CO_2$ or other acid gases.

The efficiency of a membrane depends on many factors including the pressure differential being maintained across the membrane, whereby the permeable fluid component(s) permeate to the permeate side of the membrane under a partial pressure gradient. In order to maintain the partial pressure differential across the membrane, a sweep fluid is often used to help remove the permeating fluid. The lower the partial pressure of the permeate, the better the separation. This is especially important in applications where only small amounts of fluid are to be separated from the fluid mixture. However, many uses for the permeate require further pressurization of the permeate. Low permeate partial pressure is desired for efficient membrane application, but high permeate pressure is desired to reduce compression costs.

While membrane systems that use sweep fluids have been effective in improving the efficiency of membrane separation of fluid, there is a continuing need for improving to efficiency of membrane separation processes.

SUMMARY

This invention provides a method and system for separating at least one gaseous or vaporous component from a multi-component gas stream. A flow conduit is provided having a semi-permeable section adapted to selectively permeate the at least one gaseous component to be separated in the presence of the multi-component gas flowing along one side of the semi-permeable section. The multi-component gas is passed along the feed side of the flow conduit and a sweep gas, having a first velocity, is provided for passage along the permeate side of the flow conduit, the sweep gas being suitable for sweeping the component gas that permeates through the permeable section of the conduit away from the permeate side of the flow conduit, thereby producing a gas mixture comprising the sweep gas and the component gas. The velocity of the sweep gas is accelerated so that the velocity of the sweep gas along at least a portion of the permeate side of the flow conduit is greater than to first velocity of the sweep gas. The gas mixture is then decelerated by means of a defuser, thereby recovering as pressure a portion of the energy of the gas mixture.

BRIEF DESCRIPTION OF THE DRAWINGS

The present invention and its advantages will be better understood by referring to the following detailed description and the attached drawings, in which like reference numerals are used to indicate like parts in various views.

FIG. 1 is a sectional, schematic view of one embodiment of the present invention showing a feed gas conduit with a portion of the conduit's structure being semi-permeable and a nozzle conduit surrounding a portion of the feed conduit for collecting permeate and for passing sweep gas across the semi-permeable structure at subsonic velocity.

FIG. 2 is a cross-sectional view of the embodiment shown in FIG. 1 taken along lines 2-2.

DETAILED DESCRIPTION OF THE INVENTION

Figure 3:
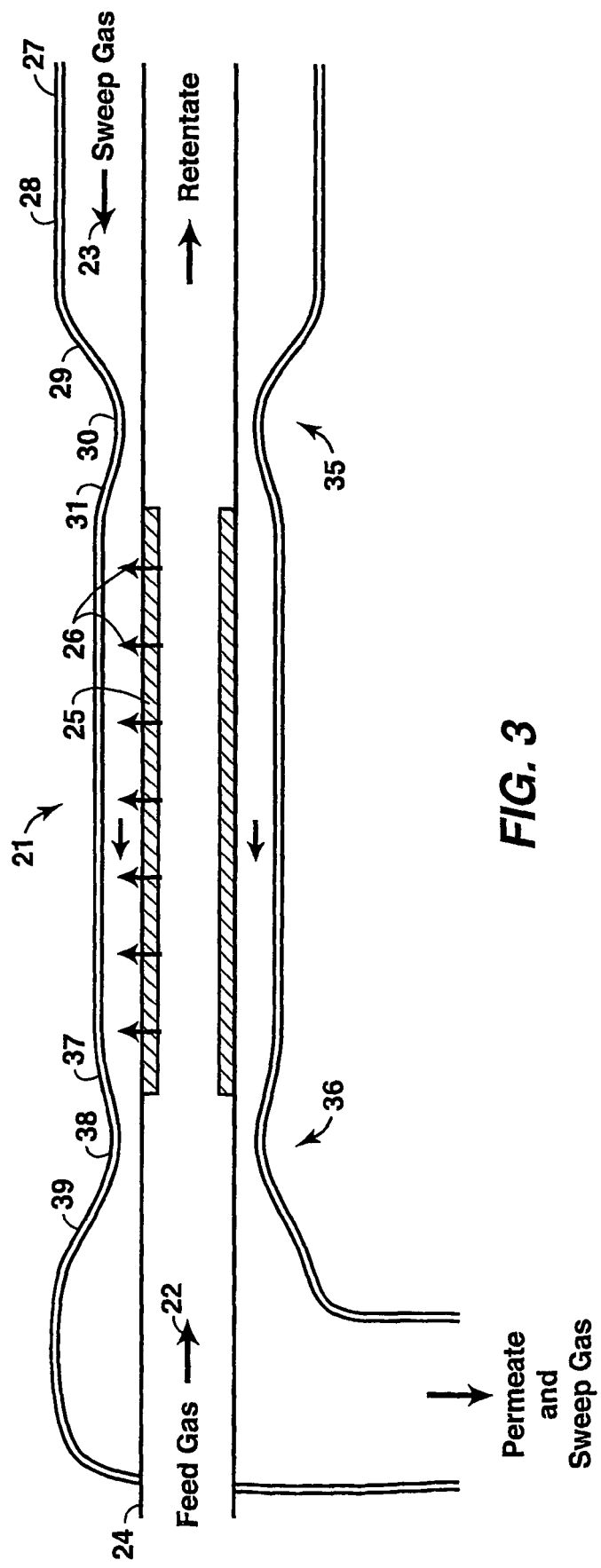
FIG. 3 is a sectional, schematic view of a second embodiment of the present invention similar to FIG. 1 except that the nozzle conduit surrounding the semi-permeable structure provides for supersonic velocity of the sweep gas across the semi-permeable structure.

The present invention provides an apparatus and method for separating one or more components from a multi-component gas using a separation system having a feed side and a permeate side separated by a semi-permeable structure. The separation system uses a sweep gas to facilitate removal of permeate from the permeate side of the separation system. This present invention increases the velocity of sweep gas on the permeate side of the semi-permeable structure by reducing the cross-sectional area of sweep gas flow, thereby increasing the velocity of the sweep gas and reducing the static pressure of the permeate on the permeate side of the structure. The reduction in static pressure is achieved in one embodiment by using a converging nozzle for subsonic flow velocities and in another embodiment by using a converging-diverging nozzle for supersonic flow velocities.

The terms used in this description are defined as follows:

"Effuser" means a flow channel having a convergent section downstream of flowing section which functions as an aerodynamic expander. An effuser may have a converging volume or a converging and then diverging volume.

"Supersonic effuser" means a flow channel having a convergent subsonic section upstream of a divergent supersonic section with an intervening sonic throat which functions as an aerodynamic expander.

"Diffuser" means a flow channel having downstream divergent section which functions as an aerodynamic compressor. A diffuser may have a diverging volume or a converging and then diverging volume.

"Supersonic diffuser" means a flow channel having a convergent super sonic section upstream of a divergent subsonic section with an intervening sonic throat which functions as an aerodynamic compressor.

"Throat" means a reduced area in a flow channel, as in an effuser or diffuser.

"Natural gas" refers to a multi-component gas obtained from a crude oil well (associated gas) or from a subterranean gas-bearing formation (non-associated gas). The composition and pressure of natural gas can vary significantly. A typical natural gas stream contains methane ($C_1$) as a significant component. The natural gas will also typically contain ethane ($C_2$), higher molecular weight hydrocarbons, one or more acid gases (such as carbon dioxide, hydrogen sulfide, carbonyl sulfide, carbon disulfide, and mercaptans), and minor amounts of contaminants such as water, nitrogen, iron sulfide, wax, and crude oil.

The present invention is particularly suitable for treatment of natural gas streams containing one or more contaminants such as carbon dioxide, hydrogen sulfide, and water vapor. However, the invention is not limited to treatment of natural gas. The inventive device and method can be used to separate multi-component gas, in which a semi-permeable membrane is used to separate one or more components of the multi-component gas.

FIG. 1 schematically illustrates one embodiment of a fluid separation device 10 of the present invention. A multi-component feed gas stream enters fluid separation device 10 through flow conduit 14. Arrow 12 shows the flow direction of the feed gas. A portion of conduit 14 has a semi-permeable structure 15 through which one or more components of a multi-component fluid stream 12 can selectively permeate therethrough. Arrows 16 show the direction of the permeate through conduit structure 15. A sweep fluid is passed through flow conduit 17 in the direction of arrow 13. Flow conduit 17 has a converging section 18 which causes the sweep gas stream to accelerate. Downstream of the converging section 18, the cross-sectional area of the sweep conduit 17 can remain constant, progressively increase or, as shown in FIG. 1, progressively decrease. By conduit 17 progressively decreasing along the length of the semi-permeable structure 15 the velocity of the sweep gas can be maintained as the permeate that mixes with the sweep gas increases the mass flow of the mixture along the length of the structure 15. The converging section 18 of conduit 17 functions as an effuser causing the pressure of the sweep gas to decrease. This reduction in pressure causes the partial pressure of permeate on the permeate side of structure 15 to be lower than the partial pressure would be if the velocity of sweep gas in conduit 17 remained at constant velocity.

After passing semi-permeable structure 15, conduit 17 is passed through a diffuser 20 which functions as a compressor. As shown in FIG. 1, downstream of point 19 of conduit 17, the cross-sectional area of the conduit 17 diverges, thereby causing the velocity of the gas mixture of permeate and sweep gas to decrease and the pressure of the mixture to increase. The diffuser 20 provides for the partial transformation of the kinetic energy of the gas mixture to an increased pressure.

FIG. 2 illustrates a sectional view of the fluid separation device depicted in FIG. 1 taken along lines 2-2. In this embodiment, conduits 15 and 17 have a circular cross-section. However, other suitable cross-sectional designs of each conduit may be selected.

FIG. 3 illustrates a sectional, schematic view of a second embodiment of the present invention similar to FIG. 1 except that sweep conduit 27 surrounds a semi-permeable structure 25 to provide supersonic velocity of the sweep gas across the semi-permeable structure 25. In the embodiment illustrated in FIG. 1, subsonic velocities are generated, but in some applications it may be desirable to generate sonic velocity in the sweep gas close to the throat of an effuser so as to cause the sweep gas to expand supersonically as the sweep gas flows along the permeate side of the gas separation device.

Referring to FIG. 3, a multi-component, gas stream enters fluid separation device 21 through flow conduit 24. Arrow 22 shows the flow direction of the feed gas. A portion of conduit 24 has a semi-permeable structure 25 through which one or more components of a multi-component fluid stream selectively permeate therethrough. Arrows 26 show the direction of permeate through conduit structure 25. A sweep fluid is passed through flow conduit 27 in the direction of arrow 23. The cross-sectional area of flow conduit 27 forms a supersonic effuser 35 having the general shape of an axisymmetric nozzle comprising a cylindrical section 28, a convergent truncated, subsonic, cone section 29, a throat 30, and a divergent, supersonic section 31. The effuser 35 is a de Laval-type of nozzle for inducing the sweep stream to flow at supersonic velocity. The cross-sectional area of the sweep conduit 27 that is concentric to the semi-permeable structure 25 is shown as being constant in FIG. 3, but optionally this portion of conduit 27 can progressively increase or progressively decrease along the length of the semi-permeable structure 25. The converging section 29 causes the pressure of the sweep gas to decrease. This reduction in pressure causes the partial pressure of permeate on the permeate side of the semi-permeable structure 25 to be lower than the partial pressure would be if conduit 27 remained at constant velocity.

After passing semi-permeable structure 25, the gas mixture of permeate and sweep gas is passed through a diffuser 36 which comprises a convergent, supersonic, truncated-cone section 37, a throat 38, and a divergent subsonic section 39. The diffuser 36 functions as a compressor, causing the velocity of the mixture of permeate and sweep gas to decrease and the pressure of the mixture to increase.

Depending on the application, any suitable rigid material can be used for the effuser 35 and diffuser 36.

Although not shown in FIG. 3, one or both of the effuser throat 30 and diffuser throat 38 can be adjustable. The geometry and size of the effuser 35 and diffuser 36 that ensure the desired velocity conditions along the permeate side of semi-permeable structure 25 can be chosen by those skilled in the art on the basis of known laws of thermodynamics of gas and the known initial data of the sweep gas flow, including for example the sweep gas pressure at the entrance to the effuser 35, the temperature of the sweep gas, and the chemical composition of the sweep gas.

The sweep gas used in the present invention can be any gas or vapor that contains a relatively low concentration of the one or more gas components to be removed from the multi-component feed gas. Nonlimiting examples of a sweep gas may include hydrogen, air, steam, carbon dioxide, carbon monoxide, and inert gases such as argon and helium.

The feed gas to the separation system 10 of FIG. 1 and the separation system 21 of FIG. 3 may derive from a variety of sources including, but not limited to, industrial process vent streams, vaporous overhead from a distillation column, the overhead from a reflux process, chemical process streams, and natural gas production from subterranean gas-bearing formations. The feed gas can comprise virtually any multi-component gas mixture with sufficient volatility to be present in the vapor phase.

The semi-permeable structure 25 for use in the present invention can be any suitable device having a selectively permeable nature and more specifically it may be any device being relatively permeable to at least one component relative to one or more other components in the feed stream. The semi-permeable structure 25 can be of any suitable design for vapor separations. Tubular structures are preferred to obtain the benefits of the partial pressure reduction on the permeate side of the membrane in accordance with this invention. The semi-permeable structure 25 can be made entirely of the permselective material or the permselective material may be supported on a porous structure, fabric, or screen. The semi-permeable structure 25 is preferably composed of a separation layer and a support with the separation layer being formed on the surface of the support. The support is designed to provide mechanical support to the separation layer while offering as little mass transfer resistance as possible. The flux through the semi-permeable structure is affected by the thickness of the separation material and the support. In general it is desirable to have the separation layer, through which a permeating component must pass, as thin as possible yet sufficiently thick that the flow through the layer is not dominated by defects. The support must be thick enough to provide adequate strength to the separation layer to withstand the separation conditions. Suitable composite semi-permeable structure may comprise a thin separation layer or membrane formed on the surface of a thicker porous physical support that provides the necessary physical strength to the membrane. The number and length of the individual membranes used in the semi-permeable structure can be varied to suit the fluid flow rates and flux requirements of particular applications.

With respect to the composition of the separation layer, substantially any semi-permeable material currently available, or which may become available, can be used. The separation layer can be either symmetric or asymmetric, isotropic (having substantially the same density throughout) or anisotropic (having at least one zone of greater density than at least one other zone), and can be chemically homogeneous (constructed of the same material) or it may be a composite membrane.

When the membrane separation systems illustrated in FIGS. 1 and 3 are used to remove contaminants from natural gas stream, the separation layer preferably is composed of material tolerant to temperatures above 120° F. (48.9° C.) and pressures above 1,200 psia (82.8 bar) and have adequate effective permeance and selectivity at those conditions. May membranes in service for acid gas removal from natural gas streams are made from polymers, and most of these polymers either lack stability at the operating conditions at temperatures above 120° F. (48.9° C.) and pressures above about 1,200 psia (82.8 bar) or do not provide adequate values of permeance or selectivity. Many of such polymeric membranes have been designed or selected to operate most effectively at temperatures below about 100° F. (37.8° C.). While certain polymers or glassy materials could give adequate performance at higher temperature and pressure conditions, it is preferred that the separation layer used in natural gas treatment be inorganic. The inorganic layer, formed from, for example, zeolites, microporous silica, or microporous carbon, is preferably placed on a structured support.

The support should offer minimal mass transfer resistance with strength sufficient to withstand the stress created by relatively large pressure differentials across the membrane. For asymmetric membranes, the support is porous. It is also possible to form an asymmetric hybrid membrane structure in which a polymeric active separation layer is coated onto a porous inorganic support. For asymmetric inorganic membranes, the porous support can be made from a different material than the active separation layer. Support materials for asymmetric inorganic membranes include porous aluminas, silicon carbides, porous metals, cordierties, and carbons. Typically for asymmetric polymer membranes, the porous support is manufactured from the some polymer as the active separation layer. In some polymer membrane manufacturing processes, the porous support material is formed simultaneously with active separation layer.

The invention is not intended to be limited to any particular separation layer or support, and the separation layer and support may comprise any material capable of giving a values for permeance and selectivity. This includes, for example, homogeneous membranes, composite membranes, and membranes incorporating sorbents, carriers, or plasticizers. Inasmuch as the composition and preparation of membrane are well known to those skilled in the art, a more detailed description thereof is not provided he FIGS. 1 and 3 illustrate embodiments in which the multi-component fluid to be treated and the sweep fluid are in countercurrent flow, which is the preferred arrangement. However, co-current arrangements could also be produced, one embodiment of which is shown in FIG. 4.

Figure 4:
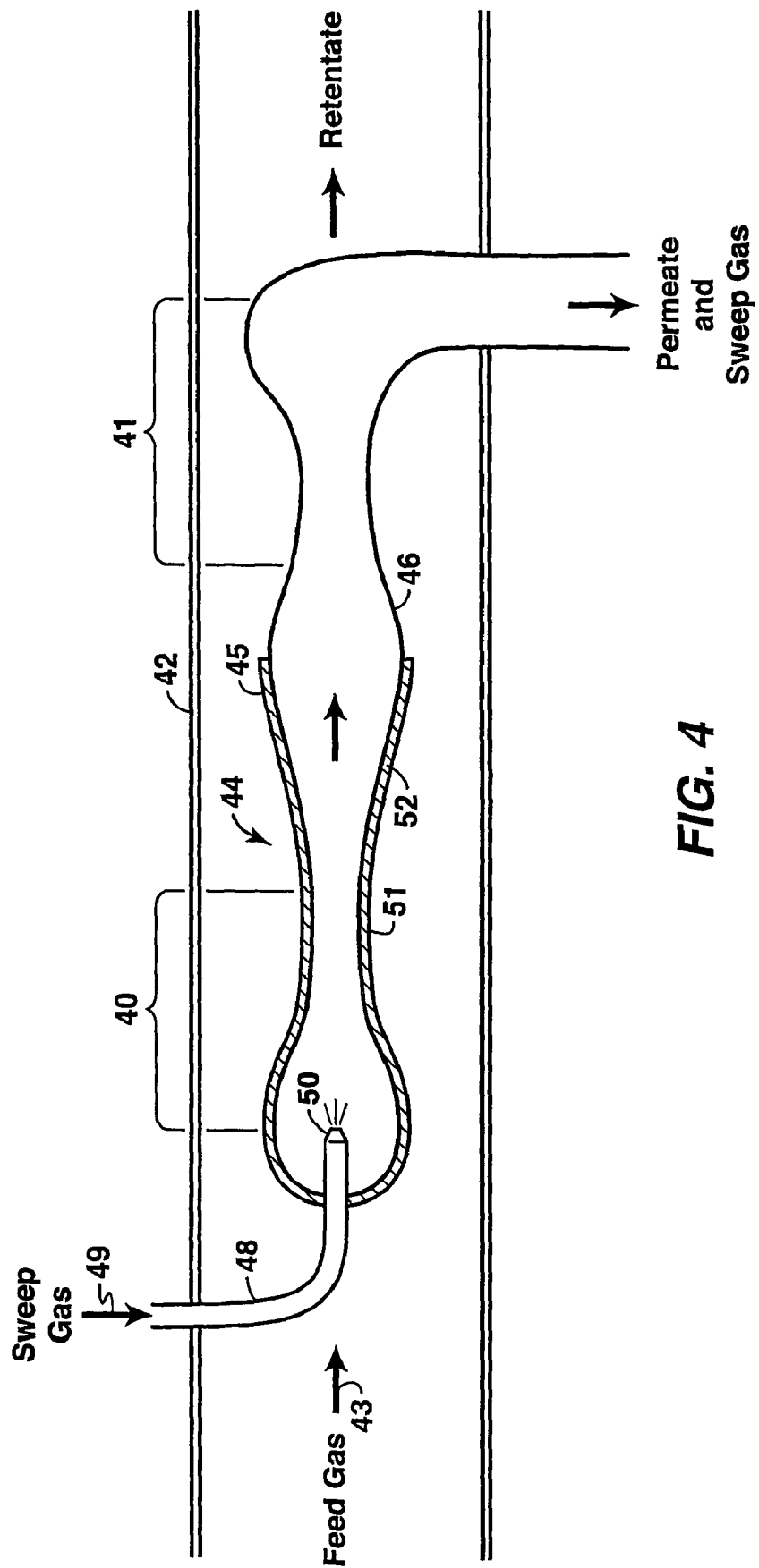
FIG. 4 is a sectional, schematic view of a third embodiment of the present invention showing a nozzle conduit on the inside of a membrane conduit, the nozzle conduit collecting permeate and providing passage of sweep fluid at subsonic velocity.

FIG. 4 illustrates a sectional, schematic view of a third embodiment of the present invention showing an effuser 40 and diffuser 41 on the inside of a multi-component feed gas stream that is passing through a flow conduit 42 in the direction of arrow 43. A semi-permeable membrane module 44 is disposed on the inside of a flow conduit 42. Membrane module 44 comprises a membrane layer 45 that is coated or bonded to the surface of a support member 46. The membrane module 44 may also include other layers not shown FIG. 4, such as a protective layer that may include for example a cage or screen to protect the outside membrane layer.

Sweep gas 49 enters the separation module through sweep gas inlet conduit 48. The direction of sweep gas 49 into conduit 48. Inlet conduit 48 passes through the bulb-shaped end of membrane module 44 and ends at nozzle 50, thereby enabling sweep gas 49 to flow through inlet conduit 48 and exit through nozzle 50. The velocity of sweep gas 49 through nozzle 50 induces a low pressure zone in the throat 51 of a vent portion 52 of the membrane module 44, drawing permeate through the membrane layer 45 to the interior of membrane module 44. A diffuser 41 is located downstream of the membrane module 44. The high velocity of the mixture of permeate and sweep gas exiting the membrane module 44 is reduced in velocity in diffuser 41 to produce an increase in pressure over that of the gas mixture through section venturi portion 52.

In FIG. 4, diffuser 41 is shown as being positioned immediately following the passage of the sweep gas past membrane module 44. However, the diffuser 41 may optionally be positioned father downstream than shown in FIG. 4. The diffuser 41 may optionally be outside conduit 42.

The method of the present invention may be practiced in any flow environment involving two or more concentric flow lines in which at least a portion of the inner conduit has a semi-permeable wall for selective permeation of one or more components of a multi-component gas stream. The concentric flow lines may be pipelines located above or below the surface of the earth or the flow lines may comprise components of a wellbore, such as a tubing string and casing in a well that produces natural gas from one or more subterranean formations.

A person skilled in the art, particularly one having the benefit of the teachings of this patent, will recognize many modifications and variations to the specific processes disclosed above. For example, a variety of temperatures and pressures may be used in accordance with the invention, depending on the overall design of the system and the composition of the feed gas. Also, the feed gas cooling train may be supplemented or reconfigured depending on the overall design requirements to achieve optimum and efficient heat exchange requirements. As discussed above, the specifically disclosed embodiments should not be used to limit or restrict the scope of the invention, which is to be determined by the claims below and their equivalents

What is claimed is:

1. A method of separating a component from a multi-component gas, comprising:
   (a) providing a flow conduit having a semi-permeable section adapted to selectively permeate the component to be separated in the presence of the multi-component gas flowing therethrough, the flow conduit having a feed side and a permeate side;
   (b) passing the multi-component gas along the feed side of the flow conduit;
   (c) providing a sweep gas at a first velocity, the sweep gas being suitable for passage along the permeate side of the flow conduit and being suitable for sweeping the component gas that permeates through the permeable section of the conduit away from the permeate side of the flow conduit, thereby producing a gas mixture comprising the sweep gas and the component gas;
   (d) accelerating the velocity of the sweep gas so that the velocity of the sweep gas along at least a portion of the permeate side of the flow conduit is greater than the first velocity of the sweep gas; and
   (e) decelerating the gas mixture by means of a defuser, thereby recovering as pressure a portion of the energy of the gas mixture.

2. The method of claim 1 wherein the multi-component gas is natural gas.

3. The method of claim 1 wherein the sweep gas is accelerated to supersonic velocity.

4. The method of claim 1 wherein the step (e) of decelerating the gas mixture is carried out by passing the gas mixture through a supersonic diffuser.

5. The method of claim 1 wherein the multi-component gas is rich in methane and contains $CO_2$ and the $CO_2$ is the component being permeated through the semi-permeable section, and the sweep gas is lean in $CO_2$.

6. A membrane separation system for separating one or more components from a multi-component gas, comprising:
   (a) a first flow conduit longitudinally positioned inside a portion of a second flow conduit, the first conduit adapted for flow of the multi-component gas therethrough, the first flow conduit having a semi-permeable membrane for permeation therethrough of one or more components of the multi-component gas;
   (b) the second conduit adapted for passage of a sweep fluid to facilitate removal of permeate on the permeate side of the membrane, the second conduit having a first area followed by a smaller second flow area, the second flow area being concentric to at least a portion of the membrane; and
   (c) the second conduit having a third flow area in a downstream direction of the second flow area, the third flow area being greater than the second flow area.

7. The membrane separation system of claim 6 wherein the second flow area continuously decreases concentrically along a substantial portion of membrane portion of the first conduit.

8. The membrane separation system of claim 6 wherein the second flow area decreases to a fourth flow area and then increases to a fifth flow area, the fifth flow area being concentric over a substantial portion of the membrane portion of the first conduit.

9. The membrane separation system of claim 8 wherein the fifth flow area decreases in area to a sixth flow area in the downstream direction of the second conduit, the sixth flow area being substantially the same at the fourth flow area.

* * * * *